United States Patent [19]
Giambernardi et al.

[11] Patent Number: 5,736,398
[45] Date of Patent: Apr. 7, 1998

[54] GAS PERMEABLE POUCHES FOR GROWING CULTURES

[75] Inventors: Troy A. Giambernardi, San Antonio; Robert J. Klebe, Helotes, both of Tex.

[73] Assignee: Board of Regents, The University of Texas System, Austin, Tex.

[21] Appl. No.: 784,452

[22] Filed: Jan. 16, 1997

[51] Int. Cl.$^6$ ............................... C12N 5/00; C12M 3/00
[52] U.S. Cl. ............ 435/383; 435/288.1; 435/304.1
[58] Field of Search ................. 435/288.1, 304.1, 435/383

[56] References Cited

U.S. PATENT DOCUMENTS 4,910,147  3/1990  Bacehowski et al. ............ 435/304.1
5,523,228  6/1996  Ingram et al. .................. 435/304.1

FOREIGN PATENT DOCUMENTS 000 47 947 A  2/1992  European Pat. Off. ......... 435/304.1

Primary Examiner—David A. Redding
Attorney, Agent, or Firm—Arnold, White & Durkee

[57] ABSTRACT

Cultures, such as bacterial, fungal, and mammalian cells and viruses of the above may be grown without agitation in culture pouch vessels having gas permeable surfaces. The culture pouches may be constructed of gas permeable silicone rubber and may include a sealable filling port and integral cuvette for measuring bacteria density. The culture pouches may be supplied with sterile dry culture medium, and culture growth may be initiated in the pouches by adding cells and sterile water.

26 Claims, 2 Drawing Sheets

GAS PERMEABLE POUCHES FOR GROWING CULTURES

The government owns rights in the present invention pursuant to grant number DE08144 from the National Institutes of Health.

FIELD OF THE INVENTION

The disclosed method and apparatus relates generally to growing cultures, particularly to growing cultures within pouches of gas permeable material. More specifically, the disclosed method and apparatus relates to growing cultures, such as bacterial, fungal, and mammalian cells, without agitation in a culture pouch having a polymeric gas permeable surface and integral cuvette.

DESCRIPTION OF RELATED ART

Growth of most organisms requires adequate amounts of oxygen. Because oxygen diffuses slowly into unstirred culture medium, growth of microbial organisms and suspension growing mammalian cells has required the use of costly agitation devices. Agitation devices facilitate the delivery of oxygen to cells grown in large volumes of culture medium. Several types of agitation methods and devices have been used to accelerate oxygen transport into culture medium. In the past, bacterial broth cultures have been aerated by, for example, rapid agitation in a shaker flask sealed with a cotton plug. Gyratory or rotary shakers and the incubators housing them are both expensive and require valuable laboratory space. The most common agitator is a gyratory platform that swirls Erlenmeyer flasks containing liter quantities of culture medium at about 200 rpm. Alternatively, several types of stirring devices have been employed. Stirring may be accomplished with a motor-driven paddle or with a motor which drives a magnetic stirring bar. In addition, agitation may be affected by bubbling air or other gases into the culture medium. The above methods and devices are typically expensive since large volumes of culture medium usually must be agitated. Moreover, mechanical agitation may be interrupted accidentally by a mechanical or human failure and may result in the loss of a culture.

Readings of the density of organisms in a culture are routinely performed during cultivation to ensure that organisms are harvested at the end of logarithmic growth. In addition, the stirring device typically must be either withdrawn or turned off when readings are taken. This is undesirable because opening and closing a culture vessel takes time and effort, in addition to exposing the culture to possible bacterial and fungal contamination. Halting agitation to take readings may also result in periodic changes in growth condition when agitation is stopped.

Passive diffusion of oxygen through certain polymeric materials has been used in the design of recent bioreactors to permit oxygen uptake into culture medium. Silicone rubber has the highest reported permeability to oxygen of known polymers (approximately 150 times as permeable) and has been used in several formats to permit transport of oxygen into a culture medium. In some designs, oxygen gas is run through silicone rubber tubing which has been placed directly into a culture medium. U.S. Pat. No. 4,897,359 and U.S. Pat. No. 4,649,114 disclose culture vessels in which oxygen is delivered to a culture medium by passive diffusion of oxygen through the walls of silicone rubber tubing. In the above designs, oxygen is available to the culture at the surface of the silicone rubber tubing; however, mechanical agitation is typically required to deliver oxygen to all cells in the culture. In addition, both of the above apparatuses employing silicone rubber tubing are complex and, therefore typically, expensive.

In other designs, sheets of silicone rubber are used to both transport oxygen and act as walls of a culture vessel. In U.S. Pat. No. 5,437,998, a tubular vessel with walls made at least partially of silicone rubber is employed. In order for this device to function, the vessel is rotated around a horizontal longitudinal central axis. Use of the device requires a means for rotating the tubular vessel, and thus the design is relatively complex and typically expensive.

In other complex designs, such as those disclosed in U.S. Pat. Nos. 5,416,022 and 4,661,455, one or more bags or envelopes constructed of silicone rubber are contained within rigid sealed housings or plates. These designs are configured to supply gases and nutrients through multiple inlets or capillary networks disposed in the housings and/or the silicone envelopes or bags. As with the designs mentioned previously, these designs are complex and expensive.

Although the devices and methods described above which permit passive diffusion of oxygen into culture medium may avoid several sources of possible contamination of cultures; mechanical stirring of cultures or complex aeration systems are required to transport oxygen from the surface of a silicone rubber aerator to cells residing at some distance from the aerator.

Accordingly, there is currently a need for new approaches to permit oxygen transport into culture medium with minimal or no mechanical stirring, and without need for complex oxygen supply systems. Moreover, there is a need to facilitate the reading of the density to which an organism has grown during cultivation without opening and closing a culture vessel.

In addition, initiation of a culture often requires sterilization of culture medium and the addition of the sterilized culture medium to a culture vessel. Therefore, sterile culture medium typically must be stored in anticipation of its use and, thus, large volumes of medium typically must be kept on hand. This is undesirable since required components of a culture medium may degrade during storage in water. Therefore, a need exists for a method and device for growing cultures which does not require bulk storage of hydrated sterile culture medium.

SUMMARY OF THE INVENTION

In one respect this invention is an apparatus for growing cultures that has a pouch formed of upper and lower surfaces comprised of gas permeable silicone rubber. At least one sealable port that extends from the pouch exterior to the pouch interior is provided in the upper surface of the pouch. The pouch also has a sealing cap which is adapted to be received by the sealable port in sealing engagement and which also has a closed end. The pouch is provided with a cuvette that has a closed end and an open end that is sealably connected to an opening defined in the closed end of the sealing cap so that the open end of the cuvette is in communication with the interior of the pouch when the sealing cap is sealably engaged with the sealable port.

In another respect, this invention is an apparatus for growing cultures that has a pouch with one or more surfaces defining a pouch interior and a pouch exterior. At least one of the surfaces of the pouch is gas permeable, and at least one port extending from the pouch exterior to the pouch interior is defined in a surface of the pouch. At least one observation or measurement device, such as an optical path length that is at least partially transparent, is disposed in communication with the interior of the pouch. The optical path length may be a cuvette. The pouch may include a port that is sealable, such as a port having a neck for receiving a cap in sealing engagement, and culture medium may be disposed within the pouch. The pouch may also include at least one surface that is a gas permeable polymer, such as silicone rubber. In some cases, the pouch may be provided with a cuvette having an open end that is sealably connected to an opening defined in a closed end of a sealing cap so that the open end of the cuvette is in communication with the interior of the pouch when the cap is engaged with the neck. The pouch and cuvette may be adapted to be received in a spectrophotometer, and the cuvette may be configured to have four sides, each side having an internal width of from about 0.1 cm to about 2 cm, and with the open and closed ends of the cuvette defining a longitudinal axis having a length of from about 1 cm to about 10 cm between the open and closed ends of the cuvette.

In another respect, this invention is a method for growing cultures including the step of providing an apparatus for growing cultures that includes a pouch having one or more surfaces defining a pouch interior and a pouch exterior. At least one of the pouch surfaces is gas permeable, and at least one port extending from the pouch exterior to the pouch interior is defined in a surface of the pouch. The method also includes the steps of introducing cells into the pouch, exposing the pouch exterior to a gas, and allowing the cells to grow within the pouch. In the practice of this method, the pouch is maintained in a static condition during cell growth and the cells are supplied with gas exclusively through the gas permeable pouch surface or by a gas pocket formed within the pouch prior to allowing the cells to grow. In addition, the cells are either supplied with no nutrients or are supplied with nutrients exclusively from a culture medium disposed within the interior of the pouch prior to allowing the cells to grow.

In another respect, this invention is a method for growing cultures, including the step of providing an apparatus for growing cultures that includes a pouch having one or more surfaces defining a pouch interior and a pouch exterior. At least one of the pouch surfaces is gas permeable, and at least one port extending from the pouch exterior to the pouch interior is defined in a surface of the pouch. The pouch also includes at least one observation or measurement device, such as an optical path length that is at least partially transparent, disposed in communication with the interior of the pouch. The optical path length may be a cuvette. The pouch may be constructed of silicone rubber. This method also includes the steps of introducing cells into the pouch, exposing the pouch exterior to a gas, and allowing the cells to grow within the pouch. In the practice of this method, the pouch may be sterilized prior to the introduction of cells into the pouch, and the cells may be agitated or maintained in a static condition during cell growth. In addition, a sterile culture medium may be disposed within the pouch, and sterile water introduced into the pouch. Cells may also be allowed to grow in the presence of a gas pocket formed within the pouch by introducing a gas into the pouch, such as oxygen, carbon dioxide, or a mixture thereof. This method may also include the step of measuring cell density within a pouch, such as by orienting a pouch equipped with a cuvette so that the cuvette is filled with growing cells, and measuring the cell density using a spectrophotometer.

DESCRIPTION OF ILLUSTRATIVE EMBODIMENTS

Figure 1:
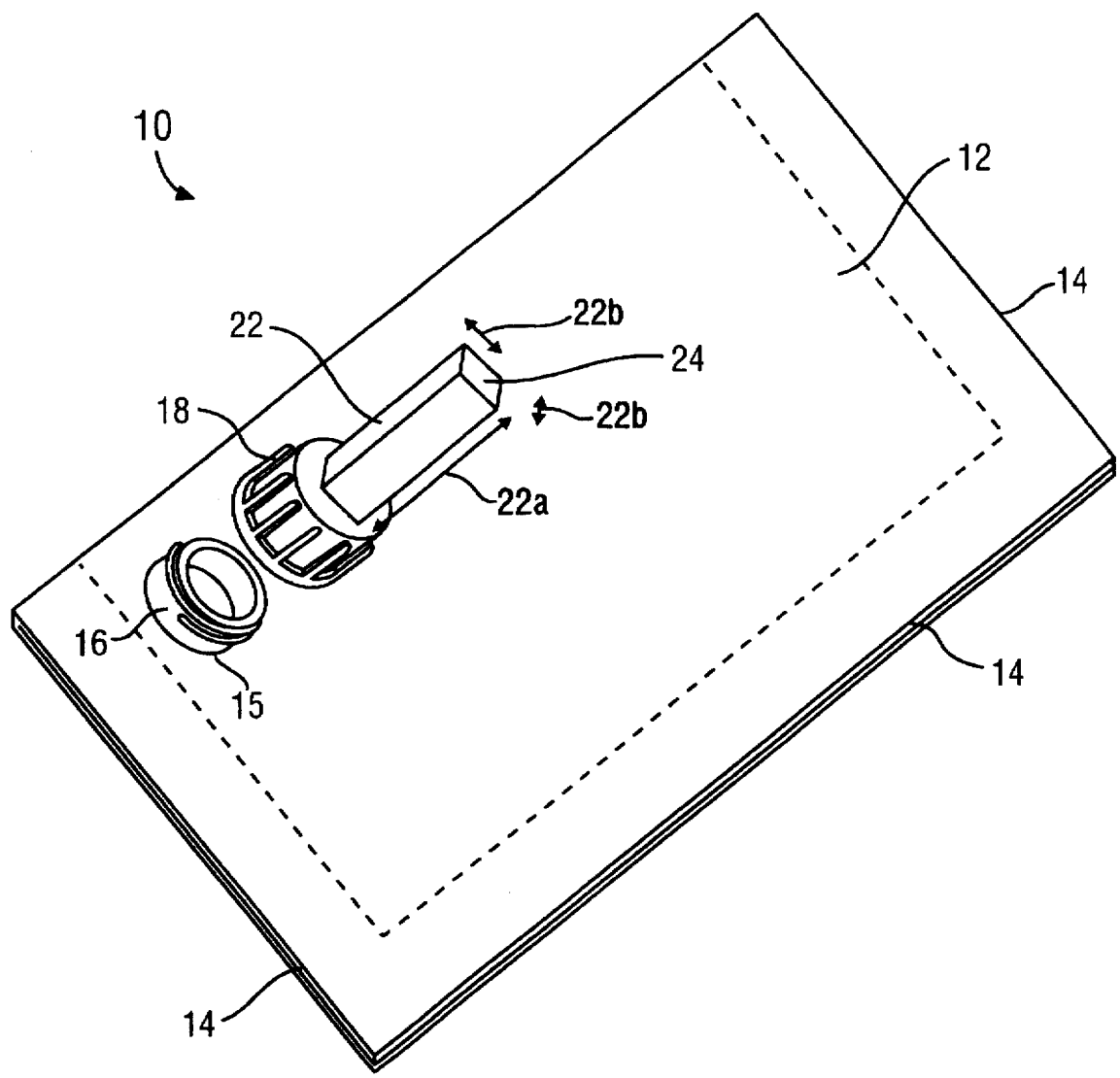
FIG. 1 shows a perspective view of a culture pouch vessel according to one embodiment of the disclosed method and apparatus.

Embodiments of the disclosed method and apparatus address deficiencies in the aforementioned art by enabling growth of cells in gas permeable culture pouches that may provide oxygenization or other essential growth parameters without the need for expensive agitation devices. These embodiments also may permit convenient measurements, such as optical readings of bacteria density, without opening a culture vessel and may permit sterile, dehydrated medium to be stored in a reusable gas permeable pouch which is inexpensive enough to be disposed of after use if desired. Other measurements may be made, for example, by employing sensors to monitor parameters including, but not limited to, concentrations of carbon dioxide, ammonia, and dissolved $O_2$ within a pouch.

Silicone rubber and other suitable gas permeable polymers used in embodiments of the disclosed method and apparatus provide means for the facile transport of oxygen and/or other gases into or away from a culture. As an example, in one embodiment of the disclosed method and apparatus, relatively small and inexpensive silicone rubber pouches may be used to grow bacteria with growth kinetics and final saturation densities that are similar to those observed using a shaker flask or other similar systems. With little or no agitation, silicone rubber pouches may produce bacterial growth rates equivalent to growth rates obtained in Erlenmeyer flasks agitated (for example, at 200 rpm) with a gyratory shaking apparatus. Silicone rubber pouches of this embodiment may also have one or more glass cuvettes integrated into their design to permit readings of bacterial density without opening a pouch, thereby saving time and minimizing risk of contamination. Advantageously, using another embodiment of the disclosed method and apparatus one may sterilize and store powdered bacterial culture medium in silicone rubber pouches so that bacterial cultures may be initiated by simply adding sterile water and bacteria. Therefore, among the advantages possible with embodiments of this disclosure are that bacteria may be grown with little, if any agitation, bacterial density may be monitored using a built-in cuvette, and cultures may be initiated by simply adding sterile water and bacteria to a pouch. In addition, when relatively small pouches are used, they take up less space and cost less than standard 2-liter glass flasks and do not require the use of other traditional equipment, such as expensive and physically large incubated gyratory shakers.

Silicone rubber has a relatively high permeability to $O_2$, $CO_2$, and $H_2O$ when compared to other known polymers. For example, the permeability (in $[cm^3][cm]/[cm^2][S][cm Hg] \times 10^{13}$) of silicone rubber to $O_2$, $CO_2$, and $H_2O$ is 367, 2430, and 32300, respectively. In comparison, the permeability of polystyrene film is 2.0, 7.9, and 840, respectively. The permeability of polyethylene is comparable to polystyrene. Thus, silicone rubber has over 100 times the $O_2$ permeability of polystyrene, polyethylene, or virtually any other polymer. Furthermore, in addition to being permeable to oxygen, carbon dioxide, ammonia, nitrogen, and other low molecular weight gases, silicone rubber may also be permeable to other volatile molecules, such as ethylene oxide. Therefore, permeability of silicone rubber and other suitable polymers to gases and bacterial waste products may allow the non-invasive removal of unwanted reagents and waste products in some embodiments. Permeability to gases other than $O_2$ and $CO_2$ has been be evidenced by the smell of *E. coli* when silicone rubber pouches have been used to grow *E. coli*.

In one embodiment of the disclosed method and apparatus, aerobic cultures grown in the interior of silicone rubber pouches of the disclosed method and apparatus may readily take up oxygen from the exterior of the pouches, and release waste gases, such as carbon dioxide, to the exterior of the pouches through permeable pouch surfaces. In another embodiment, anaerobic cultures grown in silicone rubber pouches may similarly take up carbon dioxide and release other waste gases, such as ammonia and *E. coli* odor, through permeable walls of a pouch. In still other embodiments, a culture may be exposed to or relieved from exposure to virtually any other gas or material capable of penetrating a silicone rubber pouch.

In a typical embodiment illustrated in FIG. 1, a gas permeable silicone rubber pouch 10 is fabricated from thin silicone rubber film prepared from FDA approved materials. A thin layer of silicone rubber glue is typically used to fasten one or more sheets of silicone rubber film together to form a container or pouch sealed on its edges 14. However, other methods of sealing a pouch may be employed such as, for example, by using other types of adhesives, heat, or by fabricating the pouch as one piece. One or more ports 15 are usually provided for addition of culture medium and organisms. A port 15 may be made sealable with a sealing cap, such as by providing a threaded neck 16 and complementary screw cap 18. A sealing cap may comprise any other suitable means for sealing contents of a pouch within its interior including, but not limited to, septum, poptops, stoppers, and rubber diaphragms. One or more openings may also be provided for valves and/or syringe ports.

Typically, at least one cap 18 is provided with an integral optical path length, such as a cuvette 22. The optical path length is typically between about 0.1 cm to about 2 cm in length, most typically about 1 cm inner dimension. However, an optical path length may also be of any suitable shorter or longer dimension suitable to enable spectrophotometric determination of culture density. In a typical embodiment, an optical path length is a cuvette that may be constructed of any optically suitable material, including optically transparent materials such as borosilicate glass, quartz, or transparent plastics (such as polystrene, acrylic, or polycarbonate). A cuvette may also have any suitable shape, such as square, rectangular or cylindrical and may or may not include opaque masking material. In a typical embodiment, a cuvette 22 is rectangular in shape, having four sides with each side having an internal width 22b of from about 0.1 cm to about 2 cm, most typically about 1 cm. Typical overall longitudinal length 22a of a cuvette (from its open end to its closed end) is from about 1 cm to about 10 cm, and most typically about 4 cm. In addition, a cuvette may be connected to a port or opening in a pouch in any suitable manner, including directly to a pouch without a cap. In one mode of operation, a cuvette may be filled by inverting the pouch and readings may be taken by placing the entire pouch into a spectrophotometer. In other cases, an optical path length may be constructed using a transparent spacer to separate the gas permeable surface of a pouch (typically by about 0.1 cm to about 2 cm, most typically by about 1 cm). Such a spacer may take the form of an internal transparent window within the surface of a pouch. A transparent spacer may be comprised of any suitably transparent material, such as those transparent materials previously described, and may include clear silicone rubber.

A pouch may also be configured with types of observation or measurement means or devices other than a cuvette or optical path length including, but not limited to, sensors for monitoring carbon dioxide, ammonia, dissolved oxygen, and other parameters within a pouch. Other parameters include other gases, nutrients, waste products, and properties such as temperature, pressure and the like. In addition, other ways of coupling observation or measurement devices to a pouch may be employed. For example, a remote cuvette, optical path length, sensor, or other measurement device may be connected by tubing to a pouch, or a system employing a pump may be used to pump culture fluid into a cuvette positioned inside a spectrophotometer. Like a cuvette, other types of observation or measurement means or devices may also be attached or connected directly to an opening or port within a pouch instead of a cap.

The cuvette of the pouch may be directly inserted into spectrophotometers which do not have a sample chamber lid (such as a HEWLETT PACKARD DIODE ARRAY SPECTROPHOTOMETER). The cuvette may also be inserted into other types of spectrophotometers either by not closing the sample compartment lid or by forming a suitable sized hole in the sample compartment lid capable of accepting the cuvette. In the case of an optical path length formed by a spacer separating a pouch surface, the pouch and spacer may be pressed against the opening to a monochrometer.

A pouch vessel may also be constructed of a wide variety of suitable gas permeable polymers including, but not limited to, polystyrene, polyethylene, polytetrafluoroethylene, porous polytetrafluoroethylene, porous polysulfone or polycarbonate, other porous plastics, porous plastics coated with hydrophobic material (such as silicone rubber), fabric-reinforced polymethylsiloxane, mixtures of plastics and silicone rubber, laminated silicone rubber, and cloth coated with silicone rubber. A pouch may be constructed, for example, by heat sealing one or more polymer sheets together. Typically, a 1 cm path length chamber may be provided using 1 cm long spacers in one section of the pouch.

Most desirably, a pouch is constructed in any size and configuration that provides a suitably high surface area to volume ratio for a desired culturing operation. Typically, a pouch 10 is constructed from one sheet of silicone 12 that is folded over on itself and sealed on three edges 14, as shown in FIG. 1 and described in the examples. Typical dimensions of a pouch are from about 5 inches to about 30 inches long and from about 2 inches to about 20 inches wide, with a volume of from about 50 ml to about 2000 ml. Most typically, a culture pouch for growing bacteria or yeast has dimensions of about 10 inches long by about 6 inches wide, and has a volume of about 200 ml. Other dimensions are possible. However, as dimensions and volume increase, gas transfer may be hindered if the surface area to volume ratio of a pouch decreases substantially. Therefore, it may be desirable to increase pouch volume by enlarging a pouch in a single dimensional direction only, so that the surface area to volume ratio is not reduced excessively. Because oxygen and/or other gas requirements vary with culture types, suitable pouch dimensions may vary according to culture type and/or objectives of culture growth.

One typical embodiment of the disclosed method and apparatus provides a culture vessel that permits maximal growth with little, if any, mechanical stirring. In this embodiment, pouch containers having a thickness of about 0.005 inch of silicone rubber are used to provide sufficient oxygen to permit culture growth at rates similar to that observed in shaken glass flasks and mechanically agitated silicone rubber pouches. However, other thicknesses of silicone rubber may also be successfully employed, typically from about 0.01 inches to about 0.001 inches, and more typically from about 0.004 inches to about 0.005 inches. Because mechanical shaking is not required in the present embodiment, culture methods may be simplified and problems associated with mechanical failure of motors and associated equipment are eliminated.

Advantageously, since a container of the present embodiment essentially consists of two pieces of film affixed to one another, it is much less expensive than traditional glass flasks and may be considered a disposable item. The ability to dispose of this inexpensive device after use should eliminate any possibility of contamination by bacteria or spores remaining from use on a previous occasion and also eliminates the time and cost associated with cleaning. However, it is also possible to satisfactorily clean and sterilize a container for reuse. Typically pouches may be sterilized using ethylene oxide, steam autoclaving, or another suitable method of sterilization.

A wide variety of culture types may be grown in culture pouches of the disclosed method and apparatus, including any culture capable of receiving and/or exchanging essential gases, waste gases, nutrients, and/or non-gaseous wastes through the permeable pouch surfaces. In embodiments of the disclosed method and apparatus, silicone rubber pouches are typically employed to permit growth of mass cultures with a minimum of instrumentation. Types of organisms that may be grown include, but are not limited to, bacterial, fungal, plant and animal cell cultures, as well as viruses thereof. For example, animal cells including, but not limited to, mammalian, amphibian, and avian cells may be cultured. Specific examples include, but are not limited to, hamster ovary and kidney cells, human lung fibroblast cells, monkey kidney cells, mouse embryo fibroblast cells, chick fibroblast cells, MDCK cells, vero cells. Vertebrate cell types that are typically cultured include those used in production of biological products, such as enzymes, immunity factors, hormones, anti-viral agents, vaccines, virus preparations and the like. Specific plant cells include, but are not limited to, tobacco cells, rice cells, and cactus cells. Specific aerobic bacteria that may be cultured include, but are not limited to, *E. coli.*, *subtilis*, and *S. aureus*. Specific anaerobic bacteria that may be cultured include, but are not limited to, Fusobacterium, Propionibacterium, Bacteroids, Clostridium, Lactobacillus, Peptococcus, Veillonella, and Peptostreptococcus. Specific fungal cells include, but are not limited to *S. cerevisiae*, *C. albicans*, and *C. tropicalis*.

In the practice of the disclosed method and apparatus, it is unnecessary to store culture medium containing ingredients which may degrade upon prolonged storage in water. Instead culture medium may be sterilized in pouches by, for example, ethylene oxide autoclaving or by adding sterile dehydrated medium to pouches. This allows culture medium to be hydrated only when needed. Thus, cultures may be initiated by simply adding sterile water and the desired organism to a container vessel. Advantageously, since the device may be considered a disposable item, it is possible to store dry powdered medium in the device and dispose of the device following use. This may allow, for example, preweighed and/or presterilized culture medium to be provided or sold in ready-to-use pouches, thereby reducing potential for clinical weighing errors and avoiding the need to maintain relatively large volumes of hydrated and/or sterilized culture medium on hand. Examples of suitable dry medium include, but are not limited to, LB medium, Dulbecco's medium, Murashige and Skoog medium.

Although dry culture medium is typically used, liquid culture medium may also be successfully employed. Examples of suitable liquid culture medium include, but are not limited to, LB medium, Dulbecco's medium, Murashige and Skoog medium.

In another embodiment, a growth substrate, such as tissue explant or substrate particles (e.g., collagen coated beads), may be added to a culture pouch in addition to culture medium and cells. Other types of substrates include, but are not limited to, silica particles, polystyrene balls, and reticulated polyurethane foam.

The disclosed method and apparatus also provides a simple means of growing organisms in a static condition, e.g., without need for mechanical agitation. For example, in the case of bacteria and many yeast and fungi, Brownian motion is sufficient to prevent organisms from settling to the bottom of the vessel and dying due to the generation of a high cell density of organisms at the bottom of the flask. Moreover, by provision of a modest amount of mechanical agitation, mammalian cells that grow in suspension (such as lymphocytes and some transformed cells) may be grown in the container of the disclosed apparatus.

Due to permeability it has been observed that a silicone pouch may lose 10% of its volume due to water evaporation after a 24 hour incubation at 37° C. This minor problem may be avoided by incubating the pouch underwater or in a humidified chamber. As previously mentioned, permeability of pouches to gases may result in an intense odor being emitted by bacteria grown in silicone rubber pouches. This bacterial odor may be reduced or avoided by keeping a pan of activated charcoal in an incubator.

As shown in Examples 1–5, bacterial growth in silicone rubber pouches may be equivalent to a 2-liter shaken flask and superior to other materials tested. Growth of bacteria in silicone rubber pouches may be optimized or varied by agitation (such as by shaking or stirring with a magnetic stir bar), inclusion of an air pocket, and by varying pouch surface to culture volume ratios. In addition, during the experiments of the examples, silicone rubber pouches proved to be durable and reusable with minimal care. The incorporation of a spectrophotometer cuvette into the pouch assembly allowed bacterial growth to be monitored easily.

Silicone rubber pouches are relatively inexpensive and therefore may qualify as a disposable item. Since one may store sterilized powdered bacterial culture medium in silicone rubber pouches, bacterial culture medium may be provided by suppliers in ready-to-use pouches. Culture medium may be sterilized in any suitable manner including, but not limited to, sterilization methods using ethylene oxide, gamma irradiation, heat, etc.

In still other embodiments of the disclosed method and apparatus, variations on the structure and components of a culture pouch are possible. For example, a culture pouch may be configured in any suitable shape including, but not limited to, spherical, oval, cubic, pyramidal, prismal, cylindrical, etc. A supporting structure or structures, such as of plastic, may also be employed within or outside of a pouch to provide shape and/or spacing within the pouch. A culture pouch may also be configured with more than one opening and/or multiple cuvettes, with these features being located on one or more sides.

A culture pouch may also be constructed to be only partially of gas permeable material, with the balance of the pouch being non-gas permeable, or of a varying gas permeability. Typically, a pouch is constructed to have a total surface area that is approximately 90% to about 95% gas permeable. In addition, a pouch may have a combination of gas permeable and liquid or nutrient permeable surfaces. Such surfaces include those having a porosity that is permeable to metabolic waste and medium, but impermeable to cells and substrates. In a further embodiment, a gas permeable pouch may be partially constructed with transparent materials, such as polycarbonate or clear silicone, that may allow for viewing, including viewing with a microscope or other means.

In addition, a culture pouch may also be configured to have more than one interior compartment. Pouches may be constructed with non-permeable, gas permeable, culture medium permeable, and/or waste permeable interior walls which subdivide a pouch into separate compartments such as, for example, to allow culture growth in one compartment and medium replenishment through a permeable wall from another compartment. Several pouch interiors may be linked or connected together with conduits of permeable or non-permeable material. In addition, one or more permeable or non-permeable pouch containers may be disposed within a gas permeable pouch vessel, for example, for purposes of supplying nutrients and/or gases to a culture or to facilitate removal of gases (such as by using a deoxifier) and/or other wastes.

For aerobic culture growth, suitable oxygen for growth may typically be obtained by exposure to air or other oxygen-containing mixtures, such as mixtures of air and oxygen, or mixtures of air and nitrogen. However, aerobic culture growth may be enchanced by exposure to pressurized oxygen-containing atmospheres and/or atmospheres having enhanced oxygen content. In the case of anaerobic cultures, a pouch may be placed in a controlled atmosphere having, for example, enhanced $CO_2$ and/or nitrogen content. Although it is not necessary to supply agitation or administer gases, such as oxygen or carbon dioxide, into culture pouches to grow cultures, these and other methods of stimulating or otherwise affecting growth of a culture within a culture pouch may be employed. For example, culture pouches may be configured with one or more inlets and/or internal structures (such as gas and/or nutrient permeable tubes, capillaries, hollow fibers, etc.) for supplying gases and/or nutrients to the interior of a gas permeable pouch. Similar means may also be employed for removing gases and/or wastes from the interior of a gas permeable pouch. In other cases, a culture pouch exterior may be exposed to a pressurized atmosphere and/or to incubation during culture growth for purposes of enhancing or affecting growth.

In those cases where nutrient or liquid permeable materials are used with gas permeable materials, these liquid permeable materials may include semi-porous hydrophilic and/or selectively permeable materials such as nylon, cellulose acetate, anisotropic polysulfone, saponified cellulose ester, polyethersulfone, polyacrylonitrile and acrylic copolymers.

EXAMPLES

The following examples are illustrative and should not be construed as limiting the scope of the invention or claims thereof.

Materials and Methods

Silicone Rubber Pouches. Pouches 10 were constructed as shown in FIG. 1. Silicone rubber film (cat. #S0051265301, AERO RUBBER CO., Bridgeview, Ill.) was obtained as 0.005 inch (0.127 mm) thick, 12 inch (30.48 cm) wide stock. The above material was prepared from FDA approved ingredients and has a 1200 psi tensile strength and a 500% elongation characteristic. Silicone rubber film was sealed to either itself, glass, or plastics with RTV silicone rubber glue following priming with SS4179 silicone rubber primer. A sealable filling port was constructed from a threadable neck 16 and cap 18 tube to permit facile addition of medium and bacteria. The filling port was constructed from the neck and top threaded section of a 50 ml OAK RIDGE polycarbonate centrifuge tube (cat. #3138-0050, NALGENE, Milwaukee, Wis.). Square borosilicate glass tubing (cat. #BST10150, FRIEDRICH & DIMMOCK, INC., Millville, N.J.) was cut into 55 mm lengths with a diamond band saw (GRYPHON CORP., Burbank, Calif.) to form a cuvette 22. To form a bottom 24 for the cuvette, a 13×13 mm piece of #1 microscope slides (CORNING NO. 2947) was cut with a diamond band saw. The cuvette parts were assembled with GENERAL ELECTRIC RTV 108 silicone rubber glue and GENERAL ELECTRIC SS4179 silicone rubber primer that were obtained from a local distributor. The open end of the cuvette 22 was inserted into a complementary square opening formed in the top of the screw cap 18 and glued into place with GENERAL ELECTRIC RTV 108 following priming of the cuvette 22 with GENERAL ELECTRIC SS4179 primer. Pouches were sterilized by either an ethylene oxide autoclave (MDT BIOLOGICAL CO., Rochester, N.Y.) or a steam autoclave.

During the experiments, silicone rubber pouches were cleaned by rinsing twice with distilled water, followed by two rinses with 70% ethanol alcohol and air drying. This simple washing procedure allowed the pouches to be used at least five times. It is important to note that bleaching the pouches was found to substantially reduce bacterial growth, and, thus, is not recommended.

Bacterial cultivation. Wild type E. coli K-12 was obtained from E. coli Genetic Stock Center (Yale University, New Haven, Conn.). Bacteria were grown in LB medium. An overnight culture was used to establish a starter culture that was grown to an $OD_{600}$=0.4 one hour prior to use. Shaker flask cultures were shaken in a NEW BRUNSWICK "MODEL G-10" Gyratory shaker at 220 rpm in a 37° C. room. The 2-liter flasks were capped with silicone rubber sponge closures (cat. #2004-005, BELLCO GLASS, INC., Vineland, N.J.). Silicone rubber pouches were maintained in a 37° C. incubator and were supported on 1 mm×1 mm fiberglass mesh window screens to permit aeration from both sides.

Steam autoclaved LB medium was used in most experiments. Where noted, powdered LB medium (5 g) was added to pouches and sterilized in an ethylene oxide autoclave (MDT BIOLOGICAL CO., Rochester, N.Y.) for 45 min. Ethylene oxide sterilized pouches were allowed to degas overnight and 245 ml of sterile water was added before use.

Reagents. Powered LB culture medium was obtained from SIGMA CHEMICAL CO., St. Louis, Mo. All other chemicals were reagent grade.

Procedure. In each example, a glass cuvette was integrated into the port cap to permit one to monitor bacterial growth without opening the pouch. The cuvette was filled by inverting the pouch and readings were taken by placing the entire pouch into a spectrophotometer.

A 2-liter glass flask (plus 500 ml of steam autoclaved LB media) shaken at 220 rpm with a silicone sponge closure (cat. #2004-005, BELLCO GLASS, INC., Vineland, N.J.) was used as a control for each experiment. The silicone rubber closure allowed the best growth in glass flasks compared to either a rubber stopper, aluminum foil, or a cotton-top closure (data not shown).

In all cases, growth in silicone rubber pouches was compared to growth of bacteria in 2-liter flasks shaken at 220 rpm in a NEW BRUNSWICK "MODEL G-10" Gyratory shaker at 37° C. Pouches were filled with 250 ml of LB medium with a 200 ml air pocket unless otherwise noted.

Example 1

Comparison of Pouch Materials

Figure 2:
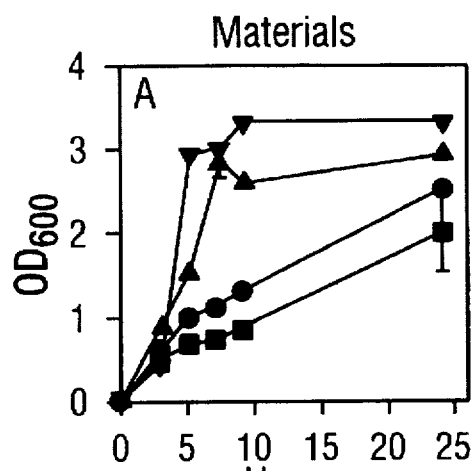
FIG. 2 is a graphical comparison of bacterial growth rate between a shaken 2-liter flask and pouch culture vessels according to various embodiments of the disclosed method and apparatus.

As shown in FIG. 2, growth in pouches constructed from silicone rubber (triangles), polyethylene (circles), or polystyrene (squares), was compared to a shaken 2-liter flask (inverted triangles). Growth in an unshaken and unstirred silicone rubber pouch was found superior to growth in polyethylene or polystyrene pouches and similar to the control shaken, 2-liter flask culture. Since bacterial growth reached saturation levels within 10 hours in both silicone rubber pouches and control shaker flasks, subsequent experiments were conducted for up to 10 hours.

Example 2

Comparison of Agitation Methods

Figure 3:
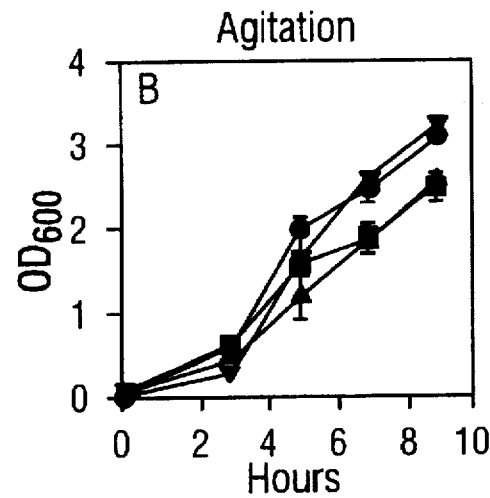
FIG. 3 is a graphical comparison of bacteria growth rate between a shaken 2-liter flask and shaken, stirred and stagnant silicone rubber pouch culture vessels according to embodiments of the disclosed method and apparatus.

As shown in FIG. 3, cultures maintained in stagnant silicone rubber pouches (triangles), silicon rubber pouches shaken at 40 rpm (squares), and silicone rubber pouches stirred with a magnetic stir bar (circles), were compared to cultures incubated in a control shaken 2-liter flask (inverted triangles). In this example, agitation of bacteria in silicone rubber pouches by magnetic stirring (63 mm stir bar at 200 rpm) improved growth to a point that was comparable to the control shaken flask. Shaking a pouch at 20–40 rpm produced bacterial growth slightly better than that observed in an unshaken, unstirred pouch. In subsequent experiments, pouch cultures were magnetically stirred at 200 rpm with a 63 mm stir bar. The results of this example demonstrate that agitating cultures at a slow rate increases bacterial growth; however, even without agitation, bacterial growth in a silicone robber pouch was to a similar final density to that obtained in shaker flasks.

Example 3

Effect of Air Volume on Growth

Figure 4:
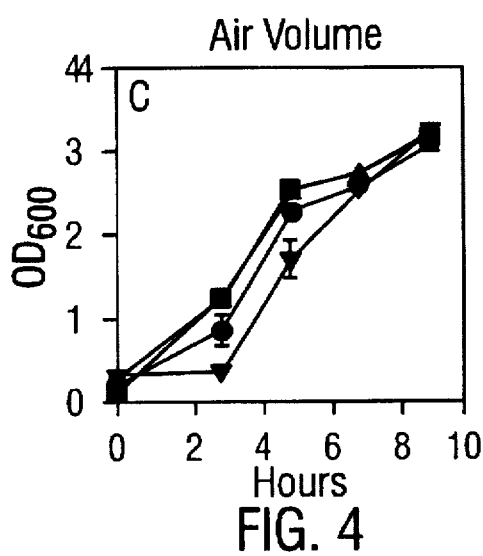
FIG. 4 is a graphical comparison of bacterial growth rate between a 2-liter shaken flask and silicone rubber pouch culture vessels according to embodiments of the disclosed method and apparatus sealed with air pockets.

As shown in FIG. 4, silicone rubber pouches were sealed with air pockets of 200 ml (triangles), 50 ml (squares), or 0 ml (circles) of air before incubation and compared to a 2-liter shaker flask control (inverted triangle). The amount of air trapped in a pouch was measured by placing a filled pouch into a large graduated cylinder, adding a known volume of water, and determining the total volume of the pouch. As seen in FIG. 4, the addition of a 50 or 200 ml air pocket to an unshaken, unstirred pouch improved growth over a pouch with no air pocket. The results of Example 3 demonstrate that inclusion of an air pocket improves growth.

Example 4

Effect of Surface Area to Volume Ratio on Growth

Figure 5:
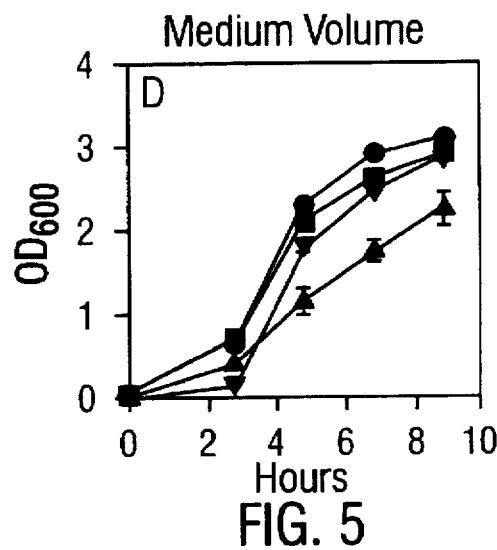
FIG. 5 is a graphical comparison between a 2-liter shaker flask and silicone rubber pouch culture vessels according to embodiments of the disclosed method and apparatus filled with varying amounts of LB medium.

As shown in FIG. 5, the surface area to volume ratio effect was examined using silicone rubber pouches of 640 cm$^2$ surface area filled with 500 ml (triangles), 250 ml (squares), and 175 ml (circles) of LB medium, and compared to a shaken 2-liter flask control (inverted triangles). A constant amount of bacteria per ml was maintained for each volume tested. As seen in FIG. 5, bacteria grew with kinetics similar to the control shaker flask in pouches with 175 and 250 ml of media. In contrast, the pouch with 500 ml of media was found to have a reduced growth rate. The results of this example indicate that, as expected, bacterial growth decreases when the area of $O_2$ permeable film per unit volume is decreased.

Example 5

Effect of Sterilization Method

Figure 6:
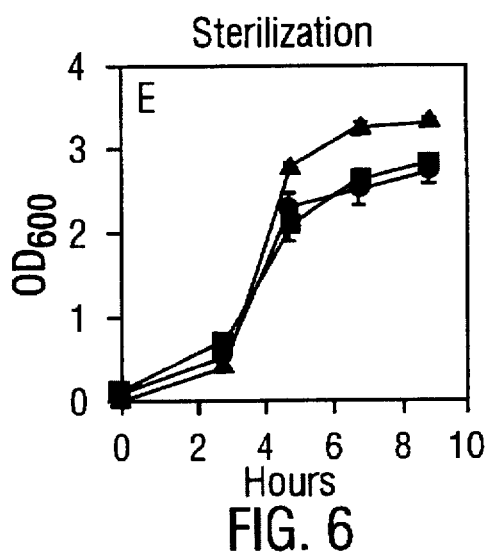
FIG. 6 is a graphical comparison of bacterial growth in LB medium between a 2-liter shaken flask and silicone rubber pouch culture vessels according to embodiments of the disclosed method and apparatus sterilized by ethylene oxide or steam autoclaving.

As shown in FIG. 6, bacterial growth in silicone rubber pouches using LB medium sterilized either by ethylene oxide (circles) or steam autoclaving (squares) was compared to growth obtained in a shaken 2-liter flask control (triangles). Ethylene oxide sterilization of dry LB powdered medium was carried out with the dry LB powder in the pouch. Sterile water was added to the pouch and then stirred. LB broth rendered sterile in this fashion was compared to growth in a silicone rubber pouch using a stirred, steam autoclaved LB solution. As seen in FIG. 6, the two sterilization methods yielded growth rates virtually identical to one another and the control shaker flask. The results of this example indicate that sterile powdered LB may be stored in sterile pouches and that bacterial growth may be initiated by simply adding sterile water and bacteria.

While the invention may be adaptable to various modifications and alternative forms, specific embodiments have been shown by way of example and described herein. However, it should be understood that the invention is not intended to be limited to the particular forms disclosed. Rather, the invention is to cover all modifications, equivalents, and alternatives falling within the spirit and scope of the invention as defined by the appended claims.

What is claimed is:

1. An apparatus for growing cultures, comprising:
   a pouch having upper and lower surfaces defining a pouch interior and a pouch exterior, the upper and lower pouch surfaces being comprised of gas permeable silicone rubber;
   at least one sealable port defined in the upper surface of the pouch, the port extending from the pouch exterior to the pouch interior;
   a sealing cap, the sealing cap having a closed end and being adapted to be received by the sealable port in sealing engagement;
   a cuvette having an open end and a closed end, wherein the open end of the cuvette is sealably connected to an opening defined in the closed end of the sealing cap such that the open end of the cuvette is in communication with the interior of the pouch when the sealing cap is sealably engaged with the sealable port.

2. An apparatus for growing cultures, comprising:

a pouch having one or more surfaces defining a pouch interior and a pouch exterior, at least one of the surfaces being gas permeable;

at least one port defined in a surface of the pouch, the port extending from the pouch exterior to the pouch interior; and at least one observation or measurement device disposed in communication with the interior of the pouch.

3. The apparatus of claim 2, wherein the observation or measurement device is an optical path length, the optical path length being at least partially transparent.

4. The apparatus of claim 3, wherein the port is sealable.

5. The apparatus of claim 3, comprising only one port.

6. The apparatus of claim 4, wherein the port has a neck for receiving a cap in sealing engagement.

7. The apparatus of claim 3, wherein at least one of the surfaces is a gas permeable polymer.

8. The apparatus of claim 3, wherein at least one of the surfaces is silicone rubber.

9. The apparatus of claim 3, wherein the one or more surfaces of the pouch are silicone rubber.

10. The apparatus of claim 3, wherein the optical path length is a cuvette.

11. The apparatus of claim 6, wherein the optical path length is a cuvette having an open end and a closed end, wherein the cap has a closed end, and wherein the open end of the cuvette is sealably connected to an opening defined in the closed end of the cap such that the open end of the cuvette is in communication with the interior of the pouch when the cap is sealably engaged with the neck.

12. The apparatus of claim 11, wherein the pouch and cuvette is adapted to be received in a spectrophotometer.

13. The apparatus of claim 11, wherein the cuvette has four sides, each side having an internal width of between about 0.1 cm to about 2 cm each, and wherein the open and closed ends of the cuvette define a longitudinal axis having a length of from about 1 cm to about 10 cm between the open and closed ends of the cuvette.

14. The apparatus of claim 3, further comprising culture medium disposed within the pouch.

15. A method for growing cultures, comprising the steps of:

providing an apparatus for growing cultures, the apparatus comprising:
a pouch having one or more surfaces defining a pouch interior and a pouch exterior, at least one of the surfaces being gas permeable;
at least one port defined in a surface of the pouch, the port extending from the pouch exterior to the pouch interior;

introducing cells into the pouch;

exposing the pouch exterior to a gas; and allowing the cells to grow within the pouch, wherein the pouch is maintained in a static condition during cell growth, wherein the cells are supplied with gas exclusively through the gas permeable pouch surface or by a gas pocket formed within the pouch prior to the step of allowing the cells to grow, and wherein the cells are either supplied with no nutrients or are supplied with nutrients exclusively from a culture medium disposed within the interior of the pouch prior to the step of allowing the cells to grow.

16. A method for growing cultures, comprising the steps of:

providing an apparatus for growing cultures, the apparatus comprising:
a pouch having one or more surfaces defining a pouch interior and a pouch exterior, at least one of the surfaces being gas permeable;
at least one port defined in a surface of the pouch, the port extending from the pouch exterior to the pouch interior;
at least one observation or measurement device disposed in communication with the interior of the pouch;

introducing cells into the pouch;

exposing the pouch exterior to a gas; and allowing the cells to grow within the pouch.

17. The apparatus of claim 16, wherein the observation or measurement device is an optical path length, the optical path length being at least partially transparent.

18. The method of claim 16, further comprising the step of maintaining the apparatus in a static condition during cell growth.

19. The method of claim 16, further comprising the step of agitating the cells within the pouch.

20. The method of claim 16, further comprising the step of sterilizing the pouch prior to introducing the cells into the pouch.

21. The method of claim 16, wherein the step of providing includes the step of providing a sterile culture medium disposed within the pouch, and further comprising the step of introducing sterile water into the pouch.

22. The method of claim 16, further comprising the steps of:

forming a gas pocket within the pouch by introducing a gas into the pouch; and allowing the cells to grow in the presence of the gas pocket.

23. The method of clam 16, wherein the gas comprises at least one of oxygen, carbon dioxide, nitrogen or a mixture thereof.

24. The method of clam 16, wherein the pouch is a silicone rubber pouch.

25. The method of claim 17, further comprising the step of measuring a density of the cells within the pouch.

26. The method of claim 25, wherein the optical path length is a cuvette and wherein the step of measuring a density of the cells within the pouch comprises the steps of:

orienting the apparatus so that the cuvette is filled with the growing cells; and measuring the cell density using a spectrophotometer.

* * * * *

Disclaimer 5,736,398—Troy A. Giambernardi, San Antonio; and Robert J. Klebe, Helotes, both of Texas. GAS PERMEABLE POUCHES FOR GROWING CULTURES. Patent dated Apr. 7, 1998. Disclaimer filed May 14, 1998, by the assignee, Board of Regents, The University of Texas System.

Hereby enters this disclaimer to claim 15 of said patent.

*(Official Gazette*, November 17, 1998)